United States Patent [19]
Dernis et al.

[11] Patent Number: 6,022,954
[45] Date of Patent: Feb. 8, 2000

[54] PROCESS FOR THE PREPARATION OF PURIFIED ALBUMIN SOLUTIONS

[75] Inventors: Dominique Dernis, Marquette-Lez-Lille; Thierry Burnouf, Wavrin, both of France

[73] Assignee: Centre Regional de Transfusion Sanguine de Lille, Lille Cedex, France

[21] Appl. No.: 07/774,745

[22] Filed: Oct. 11, 1991

Related U.S. Application Data

[63] Continuation of application No. 07/533,870, Jun. 6, 1990, abandoned.

[30] Foreign Application Priority Data

Jun. 8, 1989 [FR] France ................................ 89 07586

[51] Int. Cl.$^7$ .............................. A61K 38/00; C07G 7/00
[52] U.S. Cl. .......................... 530/364; 530/363; 530/412; 530/416; 530/427
[58] Field of Search .................................... 530/363, 364, 530/412, 416, 427

[56] References Cited

U.S. PATENT DOCUMENTS

| | | | |
|---|---|---|---|
| 3,992,367 | 11/1976 | Plan et al. | 530/369 |
| 4,086,222 | 4/1978 | Lindquist et al. | 260/122 |
| 4,228,154 | 10/1980 | Fisher et al. | 424/101 |
| 4,675,384 | 6/1987 | Dromard et al. | 530/364 |

FOREIGN PATENT DOCUMENTS

| | | |
|---|---|---|
| 0050061 | 9/1981 | European Pat. Off. . |
| 57-095997 | 6/1982 | Japan . |

OTHER PUBLICATIONS

Berglof et al., J. Appl. Biochem. vol. 5 No. 4–5, pp. 282–292 (1983).
J.M. Curling, Methods of Plasma Proteins Fractionation ed. Curling, Academic Press, London, pp. 77–91, 1980.
L. Martinache et al., Separation of Plasma Proteins ed. Curling, Pharmacia Fine Chemicals AB Upsala, Sweden, pp. 43–126, 1983.
J.M. Curling et al., Pharmacia Fine Chemicals, AB Upsala, Sweden, vol. 33, pp. 97–107, 1977.
World Patent Index Abstract, JP 57–095997 A, Nihon, Jun. 1982.

*Primary Examiner*—Cecilia J. Tsang
*Assistant Examiner*—P. Lynn Touzeau
*Attorney, Agent, or Firm*—Birch, Stewart, Kolasch & Birch, LLP

[57] ABSTRACT

The invention relates to a process for preparing purified albumin from a human or animal physiological solution, such as a plasma or a plasma fraction. The process includes a process of delipidation using an anionic detergent and two chromatographic separation stages using ion-exchange resin. By applying the process according to the invention, it is possible to obtain an albumin solution of great purity, that is stable and suitable for therapeutic use.

19 Claims, 1 Drawing Sheet

PROCESS FOR THE PREPARATION OF PURIFIED ALBUMIN SOLUTIONS

This application is a continuation, of application Ser. No. 07/533,870 filed on Jun. 6, 1990, now abandoned the entire contents of which are incorporated herein by reference.

The invention relates to the preparation of purified albumin solutions from a human or animal physiological solution, in particular through purification by ion-exchange chromatography.

Different types of processes for preparing injectable albumin solutions from the normal serum have been known for many years. These include precipitation with ethanol, using the conventional methods of Cohn or Kistler and Nitschmann, and different purification systems, including several types of chromatography columns. The starting material can be fresh or frozen plasma, a cryoprecipitate supernatant, or a fraction from which certain proteins have already been removed.

The development of a high-performance purification system has been described by Curling, Berglöf, Lindquist and Eriksson (Vox Sanguinis 33, 1977, 97–107 and in U.S. Pat. No. 4,086,222). This technology, which has been developed in particular by the Pharmacia company (Pharmacia Fine Chemicals—Uppsala—Sweden) which supplies the different types of chromatography resin, is widely used in a number of blood transfusion centers (in Europe, Canada, Australia, etc.).

However, these purification processes do not ensure the complete removal of certain contaminating molecules of a lipoprotein type, in particular α-lipoproteins, owing to their biochemical analogies with albumin.

These molecules prove unstable under heating and appear to be responsible, after denaturation, for the appearance either of particles or of a certain turbidity in the albumin solutions during pasteurization, which renders them unfit for clinical use. These contaminants are difficult to eliminate using conventional methods based on differences in molecular weight or charges. The applicants have thus developed a process for extracting and eliminating these lipoprotein contaminants that is more efficient than the additional chromatography stages described in the prior art. This process includes a stage for delipidating the albumin solution, preferably using a non-denaturing anionic detergent.

The process also preferably includes two stages of chromatographic separation using an ion-exchange resin and elution of the albumin adsorbed, the first for conventionally separating the albumin and the second being used to remove the detergent and the products resulting from delipidation and to recover a highly purified albumin solution. The latter has the advantage of being stable when pasteurized and preserved.

The delipidation treatment of the present invention consists of prolonged contact of the albumin solution eluted from the first chromatography column with an anionic detergent. This detergent can be chosen from detergents of the Tween or Triton type. In particular, very good results have been obtained with Tween 80 when its concentration is between 0.05 and 0.25 g per g of proteins and adjusted to 1 volume of Tween 80 for 8 volumes of albumin solution.

This delipidation treatment can be implemented by fairly long contact, more particularly for over 5 hours, at 25° C. or a shorter period of contact but at a higher temperature, more particularly 1 hour contact at 60° C. In the latter case, it is necessary to add an agent for stabilizing the albumin, such as sodium caprylate.

The process according to the present invention can be implemented with any physiological solution, whether human or animal, that contains albumin, as a fresh or frozen complete plasma, or as a cryoprecipitate supernatant; use can also be made of a supernatant after precipitating the plasma with ethanol according to the methods of Cohn or Kistler and Nitschmann, or a plasma fraction from which other useful proteins have already been taken. The starting material can also be derived from placenta.

Before being applied to the first chromatography column, this initial solution containing the albumin is adjusted to a protein content of between 15 and 18 g/l, a conductivity of 1.5 to 2 mS (milli-Siemens) using sodium acetate and a pH of between 5.0 and 8.0 using acetic acid or soda.

The albumin solution adjusted in this way is applied to a first chromatography column using an ion exchange resin. Good selective adsorption of the albumin is obtained with DEAE-SEPHAROSE, for example on a column of "DEAE-SEPHAROSE CL-6B fast flow" supplied by Pharmacia.

The albumin adsorbed on the chromatography column is eluted by lowering the pH of the buffer to a value of at least less than $pH_i$ (isoelectric point, approximately equal to 4.7) and more precisely between 4.0 and 4.7.

The process according to the present invention includes, after the delipidation treatment, separation on a second chromatography column, of the same type and under the same conditions as the first.

This second chromatography stage enables the Tween and the lipoprotein contaminants to be eliminated. To ensure their complete removal, the column with the adsorbed albumin is washed several times in succession with buffer solution, before the albumin is eluted by reducing the pH to a value of 4 to 4.7, as described above.

The eluted albumin solution is then adjusted to a final concentration of between 4 and 25% under physiological conditions compatible with therapeutic use and, more precisely, to a pH of between 6.5 and 7.0 and an osmolarity of 80 to 350 mosM.

The process according to the present invention then includes pasteurizing the albumin solution, previously stabilized by the addition of sodium caprylate at a concentration of 0.012 to 0.015 g/g of albumin. This pasteurization is carried out by heating at over 60° C. for at least 10 hours. After this treatment, the solutions remain perfectly clear and are stable when preserved.

According to another embodiment of the invention, the albumin solution is not pasteurized and no sodium caprylate is added to it. In this case, it undergoes virus inactivation treatment, in accordance with conventional methods, using a solvent-detergent.

The present invention also relates to the solutions of albumin purified by the process described earlier, said solutions being particularly suitable for therapeutic use.

The solutions of purified, non-pasteurized albumin can also be used to advantageously for in vitro cultures of eukaryotic cells.

The following examples serve to illustrate the invention without thereby limiting its scope.

FIG. 1 illustrates these examples and represents immunoelectrophoreses of the albumin solution before and after the delipidation treatment.

EXAMPLE 1

The starting material is, for example, a Cohn's supernatant I+II+III (after precipitation of the plasma with ethanol according to the conventional method of Cohn et al. J. Am. Chem. Soc. 68, 1946, 459–475) or its equivalent A+1 according to the conventional method of Kistler and Nitschmann (Vox Sanguinis 7, 1962, 414–424). This material is dialyzed with distilled water that has undergone osmosis (of "preparation for injection" quality).

The solution is adjusted to a protein concentration of 15 to 18 g per liter.

The pH is adjusted to 6.0 or to a value of between 5.0 and 8.0 as a function of the starting material, with acetic acid or soda. The conductivity of the solution is adjusted to 1.8 mS or to a value of between 1.5 and 2.0 mS using sodium acetate.

a. Chromatography

The solution is subjected to a first chromatography stage on a column of DEAE-SEPHAROSE CL.6B—fast flow (Pharmacia). The chromatography column is balanced with a sodium acetate buffer at a pH of 6.0. The gel is balanced when the buffer flowing from the column has a conductivity of 1.8±0.1 mS and a pH of 6.0±0.1.

The sample is injected in a proportion of 465 g of proteins for 20 liters of gel. The rate of flow is adjusted to approximately 100 l/h. After sample has been passed, return to the base line is ensured by the balancing buffer.

Lowering the pH to 5.25 then enables the transferrin to be desorbed and eluted.

The albumin is then eluted from the column by lowering the pH to a value at least less than its pHi (4.7); the acetate buffer is adjusted to a pH of 4.5 and a conductivity of 1.8 mS.

The eluted albumin solution is concentrated to approximately 100 to 150 g/l, then dialyzed with water to eliminate the acetate.

The albumin solution is then adjusted to a pH of 7.0 and an osmolarity of 250 to 350 mosM; and its concentration is adjusted either to 4 or 5% or to 20 or 25%.

b. Delipidation treatment

Sodium caprylate is added to the albumin solution in a proportion of 0.015 g of caprylate per g of proteins, as a stabilizing agent for the subsequent heating and pasteurization (when these operations do not have to be carried out, no caprylate is added). The solution is passed through a sterilizing filter.

The Tween 80 is diluted to 10% in hot sterile water in order to be incorporated into the albumin solution in a proportion of 0.5% (v/v) for a 4% albumin solution, or 2.5% (v/v) for a 20% albumin solution (the v/v are expressed in v of pure Tween/volume of albumin solution).

Then, the mixture is:

either heated at 60° C. for at least one hour, or left in contact, with gentle stirring, at 25° C. for at least 5 hours.

c. Chromatography

A column of DEAE-SEPHAROSE CL6B is used under conditions identical with those used for the first chromatography stage.

The albumin is adsorbed on the column and the Tween 80 is removed in the filtrate, together with the liquid type compounds, such as α-lipoprotein.

The column is rinsed with 10 times its buffer charge volume to ensure that the Tween 80 is completely removed.

The albumin is eluted under the same conditions as before, by lowering the pH of the buffer to 4.5.

The eluted albumin solution is then adjusted to physiological conditions, i.e. to a pH of 6.5 to 7.0 and an osmolarity of 80 to 350 mosM. The solution is filtered, placed in flasks and sterilized by heating at over 60° C. for at least 10 hours (according to the rules laid down by the pharmacopeia).

This pasteurization can be replaced by a conventional virus inactivation treatment using solvent-detergent.

EXAMPLE 2

Demonstration of the Efficiency of the Process by Immunoelectrophoresis Analysis The quality of the final albumin solution is compared with that of the solution obtained from the first chromatography column. The results are given in FIG. 1.

1A': immunoelectrophoresis in the presence of an anti-human whole plasma antiserum, prior to treatment of the albumin solution with Tween 80;

1B': immunoelectrophoresis in the presence of an anti-human whole plasma antiserum, after treatment of the albumin solution with Tween 80;

1C': same electrophoresis as in A', in the presence of an anti-ApoA specific immune serum.

Figure 1:
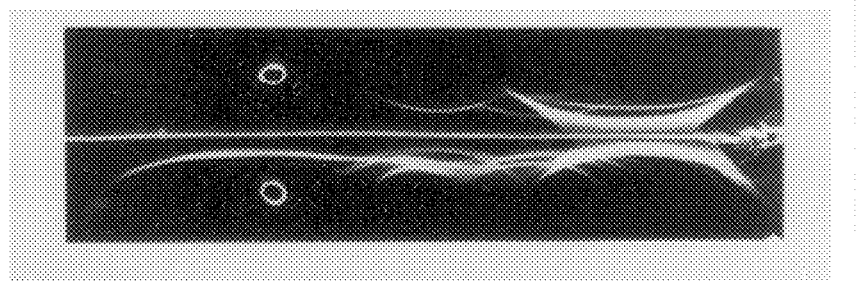
FIG. 1 represents 3 immunoelectrophoreses of albumin solutions (in the upper portion) in parallel with a control plasma (in the lower portion)
Figure 1:
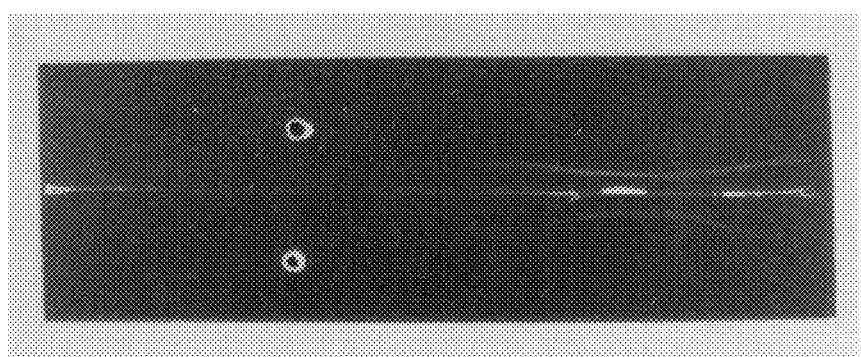

FIG. 1B' shows the disappearance of the α-lipoprotein are in the solution after treatment with Tween 80.

Figure 1C:
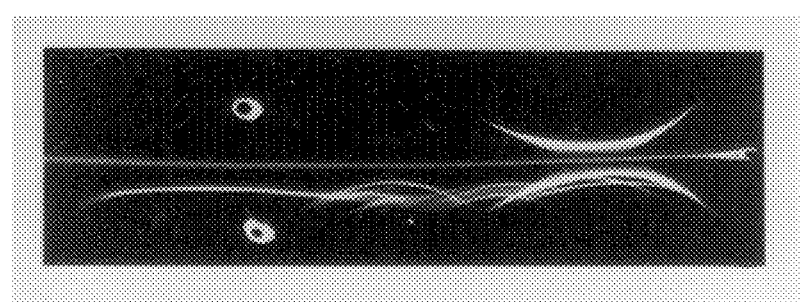

FIG. 1C' must be compared with FIG. 1A' and permits identification of the α-lipoprotein arc.

We claim:

1. A process for preparing purified albumin solution which is free from α-lipoproteins from an albumin-containing solution derived from a human or animal which comprises:

(a) contacting said albumin-containing solution derived from a human or animal with a first ion-exchange resin;

(b) eluting albumin from said first ion-exchange resin to form a first albumin solution;

(c) adding a non-denaturing anionic detergent to said first albumin solution to delipidate said first albumin solution;

(d) contacting said added non-denaturing anionic detergent to said first albumin solution with a second ion-exchange resin; and (e) eluting said albumin from said second ion-exchange resin to form said purified albumin solution.

2. The process according to claim 1, which further comprises adding sodium caprylate during step (c).

3. The process according to claim 1, which comprises adding said anionic detergent at a concentration of between 0.05 and 0.25 g per g protein.

4. The process according to claim 1, which comprises adding said anionic detergent, at a proportion of 1 volume of anionic detergent to 8 volumes of albumin.

5. The process according to claim 1, wherein said anionic detergent is Tween 80.

6. The process according to claim 1, which comprises adjusting said albumin-containing solution to a conductivity of between 1.5 and 2.5 and adjusting the pH to between 5.0 and 8.0.

7. The process according to claim 1, wherein said elution step (b) is conducted by lowering the pH to between 4 and 4.7.

8. The process according to claim 1, wherein said second ion-exchange resin is a DEAE-sepharose resin.

9. The process according to claim 1, wherein said step (d) comprises additional successive washings with a buffer solution.

10. The process according to claim 1, wherein said elution step (e) is conducted by lowering the pH to between 4 and 4.7.

11. The process according to claim 1, which further comprises adjusting said purified albumin solution to a final concentration of between 4 to 25% by weight based on the total solution.

12. The process according to claim 1, which further comprises adjusting said purified albumin solution to a pH of between 6.5 and 7.0 and to an osmolarity of between 80 to 350 mosM.

13. The process according to claim 1, which further comprises adding sodium caprylate to said purified albumin solution to a concentration of 0.012 to 0.015 g/g albumin.

14. The process according to claim 1, which further comprises heat pasteurizing said purified albumin solution.

15. The process according to claim 14, wherein said heat pasteurization is conducted at 60° C. for at least 10 hours.

16. The process according to claim 1, further comprising subjected said purified albumin solution to a viral inactivation treatment using a solvent-detergent.

17. The process according to claim 1 wherein said delipidation treatment consists of contacting said first albumin solution for a period of from about 1 hour at 60° C. to about 5 hours at 25° C. with said detergent.

18. The process according to claim 1 wherein said albumin containing solution is a complete plasma or a plasma fraction, or a cryoprecipitate supernatant or supernatant after precipitation with ethanol.

19. Process according to claim 1, which comprises adjusting said albumin containing solution to a protein content of between 15 and 18 g/l.

* * * * *